(12) United States Patent
Dahmen

(10) Patent No.: US 10,244,930 B2
(45) Date of Patent: Apr. 2, 2019

(54) POSITIONING CLIP

(75) Inventor: Jan Dahmen, Seitingen-Oberflacht (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 783 days.

(21) Appl. No.: 12/856,337

(22) Filed: Aug. 13, 2010

(65) Prior Publication Data
US 2011/0040151 A1 Feb. 17, 2011

(30) Foreign Application Priority Data

Aug. 14, 2009 (DE) .................. 10 2009 037 317

(51) Int. Cl.
A61B 1/00 (2006.01)
A61B 1/06 (2006.01)
A61B 1/07 (2006.01)
G02B 23/24 (2006.01)

(52) U.S. Cl.
CPC ............. A61B 1/07 (2013.01); A61B 1/0011 (2013.01); A61B 1/0014 (2013.01); A61B 1/00064 (2013.01); A61B 1/00071 (2013.01); A61B 1/00163 (2013.01); A61B 1/00167 (2013.01); A61B 1/06 (2013.01); A61B 1/0607 (2013.01); G02B 23/2469 (2013.01); G02B 23/2476 (2013.01); Y10T 29/49947 (2015.01)

(58) Field of Classification Search
CPC ............ A61B 1/00121; A61B 1/00124; A61B 1/00126; A61B 1/00128; A61B 1/00147; A61B 1/00064; A61B 1/00071; A61B 1/00112; A61B 1/00114; A61B 1/00117; A61B 1/00119; A61B 1/0014; A61B 1/0011; A61B 1/00163; A61B 1/00165; A61B 1/06; A61B 1/0607; A61B 1/07; Y10S 600/92

USPC ............... 600/104, 106, 115–116, 121–125, 600/156–159, 101, 102, 107, 127, 129, 600/130, 153, 154; 29/525.01; 248/74.1, 248/540, 541

See application file for complete search history.

(56) References Cited

U.S. PATENT DOCUMENTS

| 3,860,353 A | * | 1/1975 | Lukasik et al. ............... 403/351 |
| 4,286,894 A | * | 9/1981 | Rongley ................. F16C 27/04 403/372 |
| 4,569,335 A | | 2/1986 | Tsuno |
| 4,819,630 A | | 4/1989 | DeHart |
| 4,981,390 A | * | 1/1991 | Cramer, Jr. ........... F16D 1/0835 403/355 |
| 5,143,475 A | * | 9/1992 | Chikama ....................... 403/291 |
| 5,300,069 A | | 4/1994 | Hunsberger et al. |
| 5,651,759 A | | 7/1997 | Leiner et al. |

(Continued)

FOREIGN PATENT DOCUMENTS

| DE | 3929285 A1 | 3/1991 |
| DE | 19500353 A1 | 7/1996 |

(Continued)

Primary Examiner — Ryan N Henderson
(74) Attorney, Agent, or Firm — Whitmyer IP Group LLC

(57) ABSTRACT

A positioning clip to position an inner tube in an outer tube of an endoscope includes at least one inner support surface to support the positioning clip on the inner tube, at least one outer support surface to support the positioning clip on the outer tube, and a clamping device to clamp the positioning clip on the inner tube or on the outer tube.

14 Claims, 3 Drawing Sheets

(56) References Cited

U.S. PATENT DOCUMENTS

| | | | |
|---|---|---|---|
| 2002/0107530 A1* | 8/2002 | Sauer et al. .................. | 606/139 |
| 2005/0119525 A1* | 6/2005 | Takemoto ..................... | 600/114 |
| 2006/0036132 A1 | 2/2006 | Renner et al. | |
| 2006/0041186 A1 | 2/2006 | Vancaillie | |
| 2006/0199998 A1* | 9/2006 | Akui et al. .................... | 600/157 |
| 2007/0049800 A1* | 3/2007 | Boulais ......................... | 600/142 |
| 2007/0118014 A1 | 5/2007 | Fuerst et al. | |
| 2007/0185380 A1* | 8/2007 | Kucklick ....................... | 600/121 |
| 2007/0232850 A1* | 10/2007 | Stokes et al. ................. | 600/104 |
| 2007/0270788 A1* | 11/2007 | Nahen .................... | A61B 1/015 |
| | | | 606/15 |
| 2008/0277853 A1* | 11/2008 | Menn ........................... | 600/104 |
| 2009/0137875 A1* | 5/2009 | Kitagawa ............. | A61B 1/0052 |
| | | | 600/146 |

FOREIGN PATENT DOCUMENTS

| | | | |
|---|---|---|---|
| DE | 10307903 A1 | 9/2004 | |
| DE | 102005051209 A1 | 4/2007 | |
| JP | 2001017381 A | 1/2001 | |
| WO | 9315677 A2 | 8/1993 | |

* cited by examiner

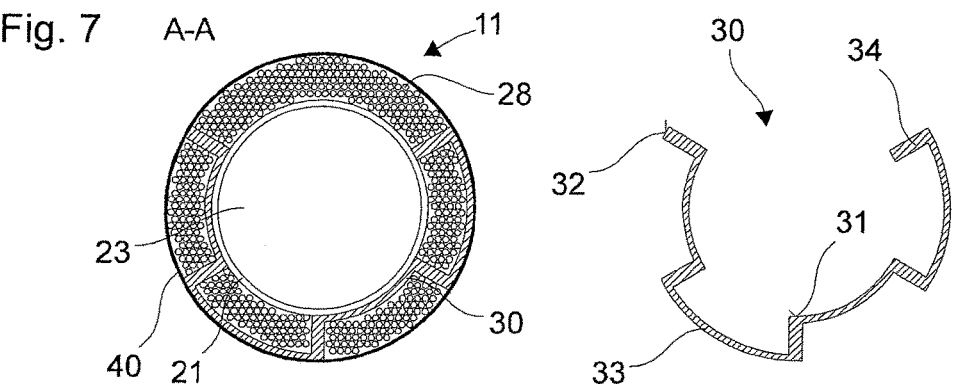
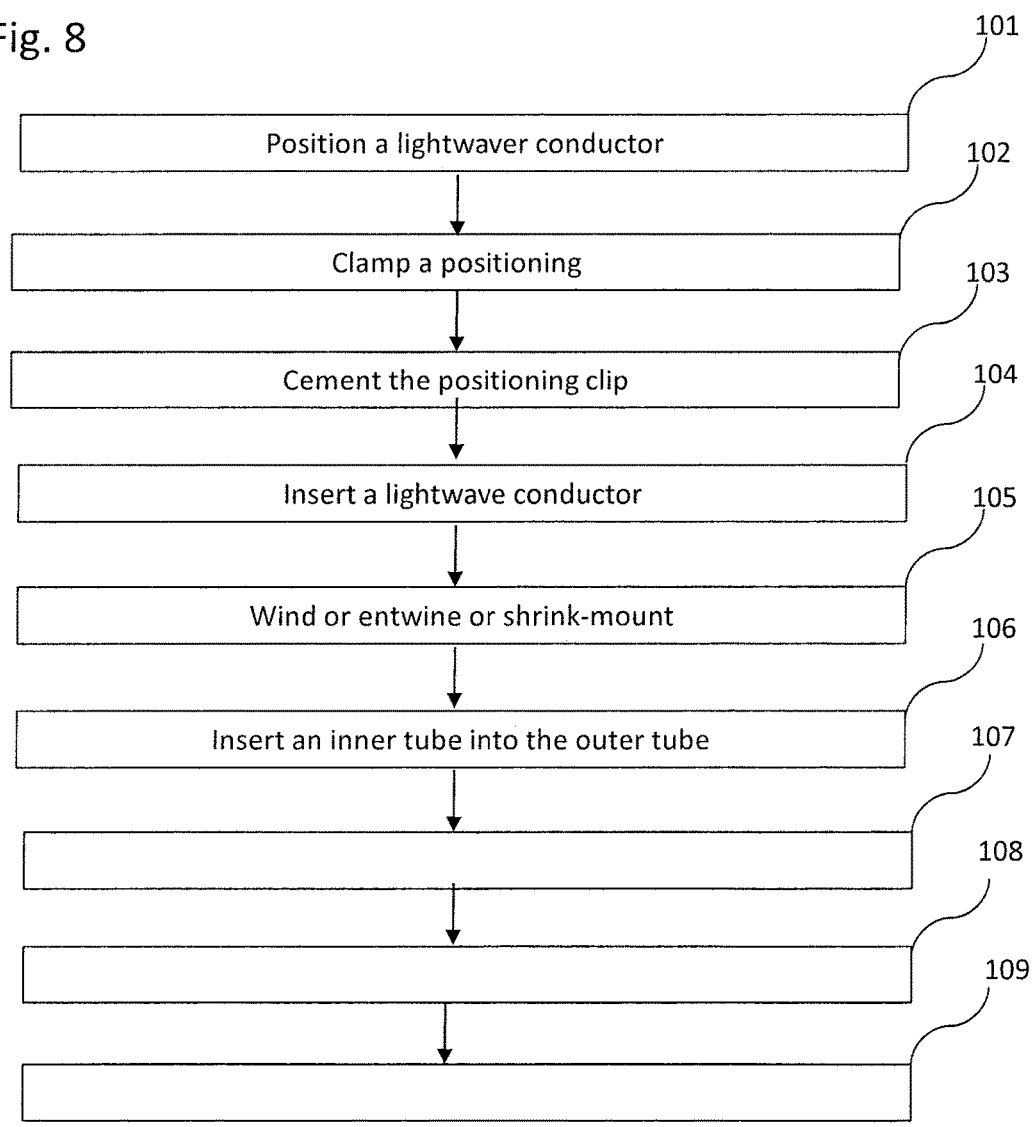

POSITIONING CLIP

CROSS-REFERENCE TO RELATED APPLICATIONS

The present application claims priority of German patent application No. 10 2009 037 317.9 filed on Aug. 14, 2009.

FIELD OF THE INVENTION

The present invention relates to a positioning clip to position an inner tube in an outer tube of an endoscope, an endoscope with such a positioning device, and a method to position an inner tube in an outer tube of an endoscope.

BACKGROUND OF THE INVENTION

The shaft of an endoscope comprises several tubes positioned inside one another. Lightwave conductors, for instance, for transmitting light for illuminating a cavity to be examined, are positioned in the hollow spaces between these tubes. During a medical procedure, the shaft of a rigid endoscope can be subjected by the medical staff to a considerable mechanical impact, in particular a bending impact. Considerable medical stresses can also arise during autoclaving because of differing thermal expansion coefficients of different components or because of temperature gradients.

Mechanical bending of a tube because of corresponding mechanical impact or also because of thermal stresses during autoclaving deforms the hollow spaces between the tubes. Lightwave conductors, electric conductors, or other functional elements positioned in the hollow spaces can thereby be pushed, stretched, compressed, squeezed, ground, or otherwise damaged. In addition, bending of the tubes and the resulting sliding of lightwave conductors can result in a one-sided, irregular illumination of the space before the distal end of the endoscope.

To avoid any deforming of hollow spaces between tubes that are positioned inside one another in a shaft of an endoscope, wire pieces or blade segments that conventionally run essentially in the longitudinal direction are welded, soldered, or cemented to the inner tube in each case. Lightwave conductors and other devices can be positioned between the wire pieces or blade segments in the interior space between the tubes. The wire pieces or blade segments service to mechanically support each of the inner tubes in each case with respect to each of the outer tubes. As a result, deformation of the hollow space is reduced and the rigidity of the shaft is increased by the distribution of mechanical stresses onto both tubes.

Positioning and joining the wire pieces or blade segments on the respective inner tube, however, is time-consuming as well as laborious and thus cost-intensive. In addition, the blade segments joined to the inner tube must then be adjusted to the inner contour of the outer tube, for instance by overwinding. In the process, the wire pieces or blade segments can again be torn off.

SUMMARY OF THE INVENTION

It is an object of the present invention to provide an improved positioning clip, an improved endoscope, and an improved method to position an inner tube in an outer tube of an endoscope.

This object is fulfilled through the content of the independent claims.

Refinements are indicated in the dependent claims.

Various embodiments of the present invention are based on the idea of clamping a positioning clip for centered or eccentric positioning of an inner tube in an outer tube of an endoscope on the inner tube or on the outer tube. Here the conventional firmly bonded connection is replaced by a force-fitted connection. In the process, the positioning clip encloses the inner tube, in particular more than halfway. The clamping occurs as a result of the elasticity of the positioning clip. The entire positioning clip, or particular elastic segments of it because of their shape, form a clamping device. The positioning clip is therefore configured for clamping to the inner tube or in the outer tube.

As a result of the clamping, the positioning clip can be installed in the shortest possible time and then can still be adjusted. The geometric shape of the positioning clip can be precisely adjusted during manufacture. Unlike with welding, soldering, or cementing, in the plain clamping foreseen here, the geometric shape of the positioning clip is maintained. In particular, the position of the outer contour of the positioning clip after the clamping is precisely defined, because the positioning clip is not partially melted and also no solder or cement can intrude between the positioning clip and the inner tube. Overwinding, as with wire pieces or blade segments joined to the inner tube by conventional means, is not required. Altogether, the result is a clearly reduced expenditure in positioning an inner tube in an outer tube by means of the positioning clip described here. In addition, contrary to the prior art, the positioning clip can first be clamped in the outer tube before the inner tube is inserted into the outer tube.

A positioning clip to position an inner tube in an outer tube of an endoscope includes at least one inner support surface for supporting the positioning clip on the inner tube, at least one outer support surface for supporting the positioning clip on the outer tube, and a clamping device for clamping the positioning clip on the inner tube or on the outer tube.

The positioning clip is configured in particular to enclose the inner tube more than halfway. The positioning clip can comprise several inner support surfaces spaced apart from one another and/or several outer support surfaces spaced apart from one another. One or more inner support surfaces and one or more outer support surfaces can be opposite one another in radial direction. Alternatively, at least one inner support surface and at least one outer support surface are positioned in alternating manner in the peripheral direction, in such a way that inner support surfaces and outer support surfaces overlap only slightly or not at all in the peripheral direction. In this and other cases, one or more links in the radial direction can each connect an inner support surface and an outer support surface. A positioning clip, in particular, comprises at least three such links as actual support segments between inner and outer tubes, so that the distance between neighboring links in particular is less than 180 degrees in each case, and advantageously about 120 degrees or less.

If the positioning clip comprises only an inner support surface or only an outer support surface, said surface extends in the peripheral direction, in particular by more than 180 degrees. If the positioning clip comprises several inner support surfaces, the distance between the edges of the closest inner support surfaces opposite to one another is in particular less than 180 degrees or less than 120 degrees, possibly with reference to an axis of symmetry of the inner tube. If the positioning clip comprises several outer support surfaces, the distance between opposite facing edges of the closest neighboring outer surfaces is in particular less than 180 degrees or less than 120 degrees, possibly with reference to an axis of symmetry of the outer tube.

An endoscope comprises one or more of the positioning clips described above. A shrink hose can be shrink-mounted onto the outer tube and positioning clip. The inner tube and positioning clip can be wrapped up or entwined, in particular by one or more threads, wires, bands, or thread-, wire-, or band-type devices.

With a method to position an inner tube in an outer tube of an endoscope, a positioning clip is first clamped on the inner tube or in the outer tube, so that the positioning clip comprises an inner support surface for support on the inner tube and an outer support surface for support on the outer tube. After the positioning clip is clamped, the inner tube is positioned in the outer tube. In an additional step before or after clamping of the positioning clip, a lightwave conductor can be positioned on the outer wall of the inner tube or on the inner wall of the outer tube. In addition, during clamping or after clamping, the positioning clip can be firmly bonded with the inner tube or the outer tube, for example by cementing or soldering. After clamping the positioning clip on the inner tube, in particular possibly before or after positioning a lightwave conductor on the outer wall of the inner tube, a shrink hose can be shrink-mounted onto the inner tube and positioning clip. Alternatively or in addition, the inner tube and positioning clip can be wrapped up or entwined, for instance by means of one or more threads, wires, bands, or thread-, wire-, or band-type devices.

The foregoing invention can be applied in particular with an inner tube and outer tube each having circular cross-section, but it can also be applied to tubes with elliptical, rectilinear, or other types of cross-section. Here the tube with the smaller cross-section is designated as the inner tube, and the tube with the great cross-section as the outer tube. In addition, the endoscope can comprise one or more tubes inside the outer tube and/or a tube in which the outer tube is positioned.

BRIEF DESCRIPTION OF THE DRAWINGS

Hereinafter embodiments are more closely explained with reference to the appended images, which are as follows.

FIG. 7 shows a schematic depiction of cross-sections of a shaft of an endoscope and of a positioning clip.

FIG. 8 shows a schematic flow diagram.

DETAILED DESCRIPTION OF THE INVENTION

Figure 1:
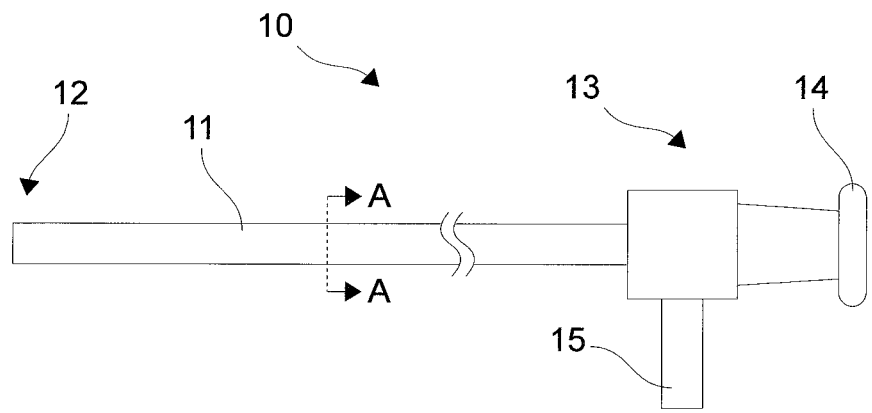
FIG. 1 shows a schematic depiction of an endoscope.

FIG. 1 shows a schematic depiction of an endoscope 10 having, in particular, a cylindrical or circular-cylindrical shaft 11, a distal end 12, and a proximal end 13. On the proximal end 13 the endoscope 10 comprises an eyepiece 14 and a coupling 15 to couple light from a light source. The endoscope 10 can comprise additional devices, which are not shown in FIG. 1.

Figure 2:
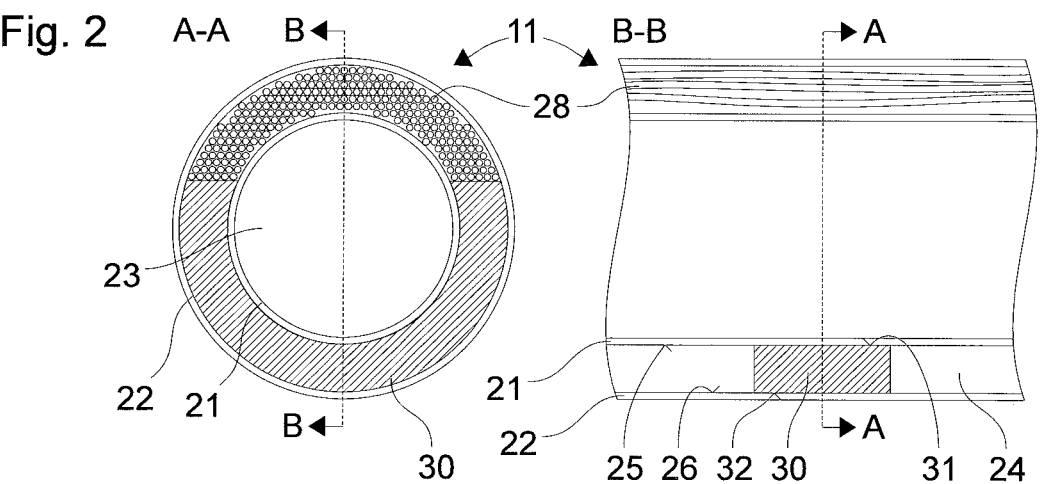
FIG. 2 shows a schematic depiction of a cross-section and a longitudinal section of a shaft of an endoscope.
Figure 3:
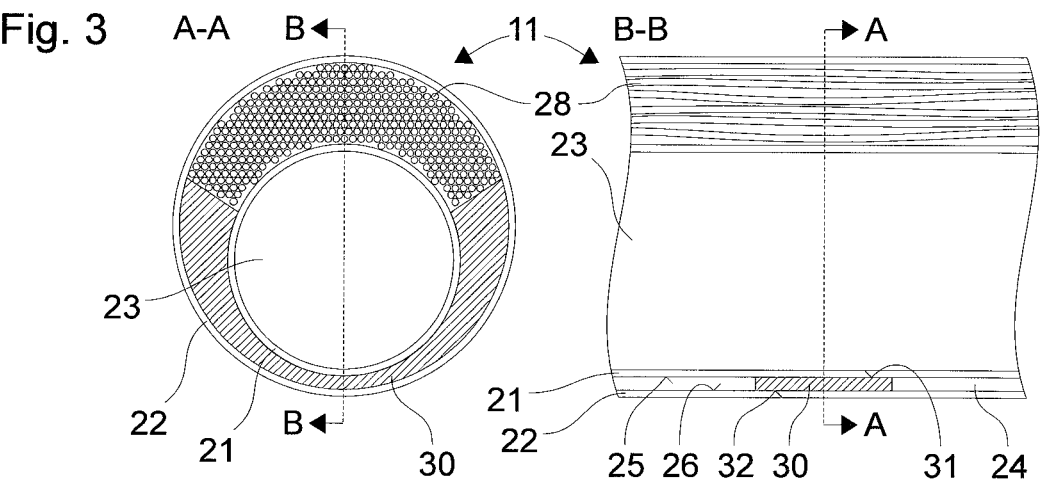
FIG. 3 shows a schematic depiction of a cross-section and a longitudinal section of a shaft of an endoscope.

FIGS. 2 through 7, discussed in the following, show sections in each case along the A-A plane shown in FIG. 1 through various embodiments of the shaft 11. The plane A-A in all cases lies perpendicular to the axis or to the longitudinal direction of the shaft 11. FIGS. 2 and 3 each show schematic views of cross-sections and longitudinal sections through the shaft 11 of an embodiment of the endoscope 10 presented above with reference to FIG. 1. To the left in each case, a cross-section is shown along the plane A-A, and to the right a longitudinal section along the plane B-B, which contains the axis of the shaft 11. The shaft includes in each case an inner tube 21, positioned in an outer tube 22. A rod lens system is positioned, for instance, in a lumen 23 of the inner tube 21 but is not shown in the illustrations. The shaft 11 can, in addition, comprise an additional tube in the lumen 23 of the inner tube 21 and/or an additional tube, which surrounds the outer tube 22.

Lightwave conductors 28 and a positioning clip 30 are positioned in an intermediate space 24 between an outer surface 25 of the inner tube 21 and an inner surface 26 of the outer tube 22. It can be recognized in the cross-sections A-A that the positioning clip 30 encloses the inner tube in each case more than halfway. An inner support surface 31 of the positioning clip 30 is contiguous in a connecting area with the outer surface 25 of the inner tube 21, which includes more than half of the outer periphery of the cross-section of the inner tube 21. An outer support surface 32 of the positioning clip 30 is contiguous in a connecting area with the inner surface 26 of the outer tube 22, which includes more than half of the inner periphery of the cross-section of the outer tube 22. The area of the intermediate space between the inner tube 21 and the outer tube 22 that is not taken up in the illustrated cross-section A-A by the positioning clip 30 is taken up by lightwave conductors 28 running in the longitudinal direction of the shaft 11.

It can be recognized in each case in the longitudinal section B-B that the measured length of the positioning clip 30 is smaller each time than the outer diameter of the inner tube 21. The positioning clip 30, however, contrary to the depictions in FIGS. 2 and 3, can be greater in length than the outer diameter of the inner tube 21. In particular, the length of the positioning clip 30 can be a multiple of the outer diameter of the inner tube 21 or a multiple of the inner diameter of the outer tube 22. In addition, the positioning clip 30 can extend over at least a fourth, a third, a half or the entire length of the shaft 11.

In the embodiment of the endoscope shown in FIG. 2, the inner tube 21 and the outer tube 22 are mounted coaxially or concentrically on one another. The positioning clip 30 thus has altogether approximately the shape of an incomplete circular ring with a square cross-section.

In the embodiment of the shaft 11 of the endoscope 10 shown in FIG. 3, the inner tube 21 is positioned eccentrically to the outer tube 22. The axes of symmetry of the inner tube 21 and of the outer tube 22 are parallel to one another and at a distance from one another. The distance between the outer surface 25 of the inner tube 21 and the inner surface 26 of the outer tube 22 therefore varies in the peripheral direction. Another consequence of the eccentric arrangement of inner tube 21 and outer tube 22 is that the space remaining for the lightwave conductors 28 is greater. Therefore, in comparison to the embodiment described above with reference to FIG. 2, more lightwave conductors 28 can be positioned between the inner tube 21 and the outer tube 22.

The positioning clips 30 described above with reference to FIGS. 2 and 3 as an overall surface including the inner support surface 31 are each contiguous with the outer surface 25 of the inner tube 21, and including their outer support surface 32 are contiguous with the inner surface 26 of the outer tube 22. In the following embodiments, presented with reference to FIGS. 4 through 7, either the inner support surface 31 or the outer support surface 32 is clearly smaller.

FIGS. 4 through 7 show schematic views of cross-sections A-A of variants of the shaft 11 of the endoscope 10 described above with reference to FIG. 1. Each of FIGS. 4 through 7, on the left in each case, depicts a cross-section of the entire shaft 11 and, on the right, a cross-section only of the positioning clip 30.

Figure 4:
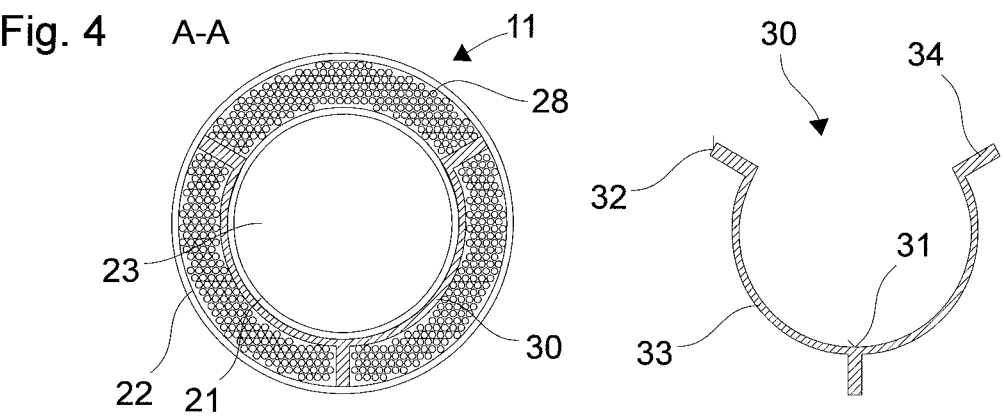
FIG. 4 shows a schematic depiction of cross-sections of a shaft of an endoscope and of a positioning clip.
Figure 5:
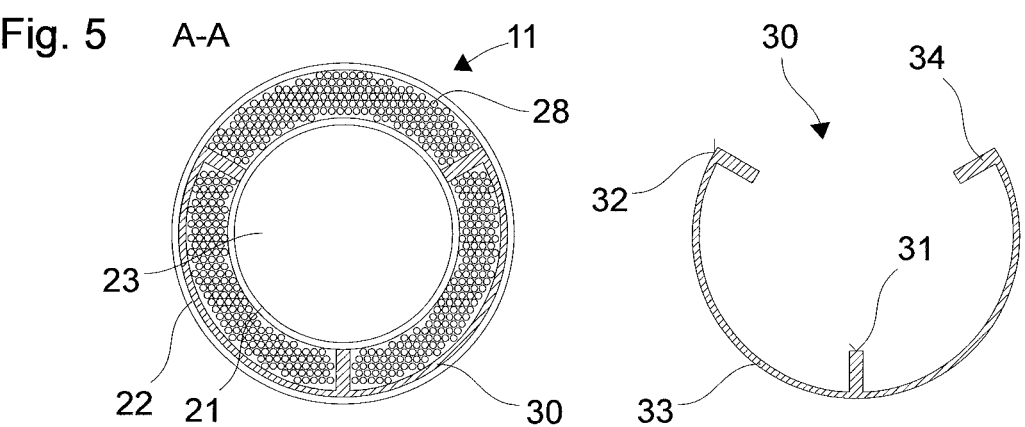
FIG. 5 shows a schematic depiction of cross-sections of a shaft of an endoscope and of a positioning clip.

In the variants shown in FIGS. 4, 5, and 7 the inner tube 21 and outer tube 22 are mounted coaxially to one another, similarly as with the embodiment shown above in FIG. 2. In the embodiment illustrated in FIG. 6 the axes of symmetry of the inner tube 21 and of the outer tube 22 are parallel to one another and at a distance from one another, similarly as with the embodiment shown above in FIG. 3.

The embodiment shown in FIG. 4 differs from the embodiment shown above in FIG. 2 in that the positioning clip 30, instead of one connecting outer support surface, has three small outer support surfaces 32. Said surfaces are connected by links 34 with a larger, connecting inner support surface 31. The links 34 are essentially positioned radially and are spaced apart from one another by about 120 degrees. Arc-shaped segments of the support device 30 between the links 34 constitute segments of a clamping device 33 because of their elastic properties.

The inner support surface 31 is larger or essentially larger than the three outer support surfaces 32 together. Therefore the static friction between the inner support surface 31 and the outer surface 25 of the inner tube 21 is greater or essentially greater than the static friction between the outer support surfaces 32 and the inner surface 26 of the outer tube 22. This can be enhanced by a corresponding pre-tensing of the positioning clip 30 or of the clamping device 33. As a result, the positioning clip shown in FIG. 4 is especially suitable for clamping on the inner tube 21 before the insertion of the inner tube 21 into the outer tube 22.

The embodiment shown in FIG. 5 is distinguished from the embodiment described above with reference to FIG. 2 in that instead of one large, connecting inner support surface, three small inner support surfaces 31 are provided. A single large connecting outer support surface 32 is connected by three links 34 with each of the inner support surfaces 31. Each of the links 34 is essentially positioned radially. The distance between each two links is approximately 120 degrees. Arc-shaped segments between the links 34 constitute segments of a clamping device 33 because of their elastic properties.

The outer support surface 32 is larger or essentially larger than the three inner support surfaces 31 together. Therefore the static friction between the outer support surface 32 and the inner surface 26 of the outer tube 22 is greater or essentially greater than the static friction between the inner support surfaces 31 and the outer surface 25 of the inner tube 21. This can be enhanced by a corresponding pre-tensing of the positioning clip 30 or of the clamping device 33. As a result, the positioning clip shown in FIG. 5 is especially suited for clamping in the outer tube 22 before the insertion of the inner tube 21 into the outer tube 22.

Figure 6:
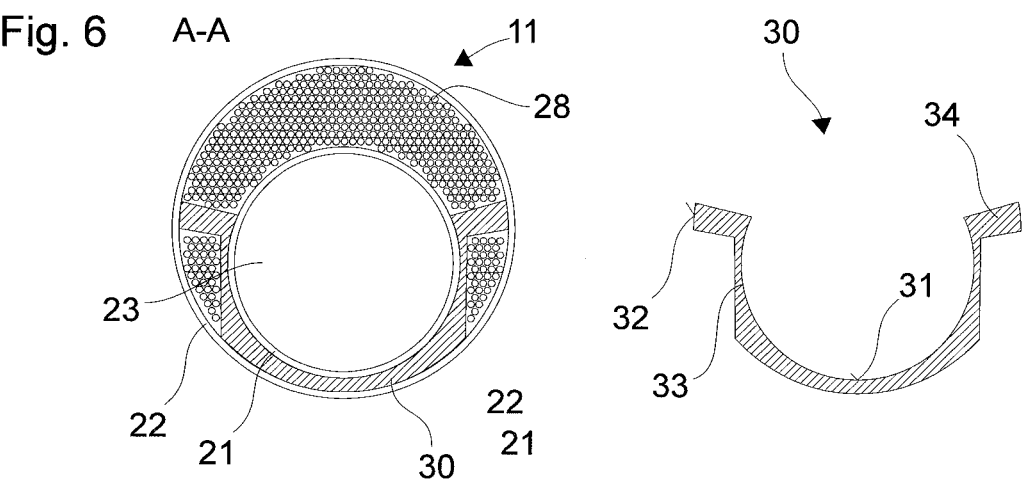
FIG. 6 shows a schematic depiction of cross-sections of a shaft of an endoscope and of a positioning clip.

The embodiment shown in FIG. 6 is distinguished from the embodiment described above with reference to FIG. 3 in that the outer support surface 32 is interrupted at two places. One end of the inner support surface 31 is connected to each of two ends of the positioning clip 30 by a link 34 with a small outer support surface 32. The two links 34 are each positioned essentially radially. In a central area the inner support surface 31 and a large outer support surface 32 are only at a small distance from one another because of the eccentric arrangement of the inner tube 21 and outer tube 22.

Similarly as with the embodiment described above with reference to FIG. 4, the inner support surface 31 is clearly larger than the outer support surfaces 32 together. Thus the static friction between the inner support surface 31 and the outer surface 25 of the inner tube 21 is greater than the static friction between the outer support surfaces 32 and the inner surface 26 of the outer tube 22. Therefore the positioning clip shown in FIG. 6 is especially suited for clamping on the inner tube 21 before the insertion into the outer tube 22.

FIG. 7 shows an embodiment that differs from the embodiments described above with reference to FIGS. 4 and 5 in that several inner support surfaces 31 at a distance from one another in peripheral direction and several outer support surfaces 32 at a distance from one another in peripheral direction are positioned in alternation. In each case, links 34 in essentially radial direction connect an inner support surface 31 and an outer support surface 32. Bent segments of the positioning clip 30 between the links 34 constitute segments of a clamping device 33 because of their elasticity.

The depiction in FIG. 7 differs from those in FIGS. 2 through 6, in addition, in that instead of the outer tube a mantle 40 is shown, which encloses the inner tube 21 with the positioning clip 30 and the lightwave conductors 28. The mantle 40 fastens the positioning clip 30 and the lightwave conductors 28 on the inner tube 21 before the inner tube 21 with the positioning clip 30 and lightwave conductors 28 is inserted into the outer tube, which is not shown in FIG. 7. The mantle 40 is, for instance, a shrink hose, which is shrink-mounted onto the positioning clip 30 and the lightwave conductors 28. Alternatively, the mantle is produced by winding or entwining the inner tube 21, the positioning clip 30, and the lightwave conductors 28 with a thread, a wire, a band, or a thread, wire, or band-type device, for instance.

It is conceivable that the positioning clips described above with reference to FIGS. 4 through 7 each take up a smaller portion of the intermediate space between the inner tube 21 and the outer tube 22 than do the positioning clips 30 described above with reference to FIGS. 2 and 3. Therefore more room remains for the lightwave conductors 28, electric lines or cables, and other devices than with the embodiments described above with reference to FIGS. 2 and 3.

Positioning clips 30, as described above with reference to FIGS. 2 through 7, can be distributed in any number over the length of the shaft 11 of an endoscope 10. For many applications, it is advantageous to place a positioning clip in the center of the shaft 11 (in relation to the longitudinal direction of the shaft 11). Especially in the case of long shaft 11, several positioning clips 30 can be provided, distributed over its length. The distances between neighboring positioning clips can be equal or can differ from one another. For example, at the center of the shaft 11 smaller distances between the positioning clips 30 can be allowed than on the distal end 12 or the proximal end 13.

A positioning clip 30, as described above with reference to FIGS. 2 through 7, comprises for instance a plastic or metal and is produced, for instance, by a casting method or by a machining method (in particular, turning or milling). It can also be advantageous to produce it from a corresponding profile (for instance, extruding profile), which is sawed or cut up into sections of corresponding length.

With all the aforementioned embodiments, the shaft 11 of the endoscope 10 has a circular cross-section. The aforementioned positioning clips, however, are also suited for an endoscope with a shaft and with inner and/or outer tubes that are not cylindrical.

FIG. 8 shows a schematic flow diagram for a method to position an inner tube in an outer tube of an endoscope. Although this method is also applicable with positioning clips and endoscopes that differ from those shown above in FIGS. 1 through 7, hereinafter use is made by way of example of reference numerals from FIGS. 1 through 7 to facilitate clarity.

In a first step 101, a lightwave conductor 28 is positioned on an inner tube 21. In a second step 102, a positioning clip 30 is clamped onto the inner tube 21. In the process, the lightwave conductor or conductors 28 positioned on the inner tube 21 in the first step 101 are at least loosely attached on the inner tube 21.

In an optional third step 103, the positioning clip 30 is fastened to the inner tube 21 by cementing, welding, soldering, or by other method.

Alternatively to the first step 101 or in addition to it, in a fourth step 104 after the third step 103, lightwave conductors 28 are positioned on the inner tube 21. Here the lightwave conductors can be positioned between the inner tube 21 and the positioning clip 30 or the positioning clip 30 can be placed between the inner tube 21 and the lightwave conductors 28.

In an optional fifth step 105, a mantle is formed around the inner tube 21, the positioning clip 30, and the lightwave conductor or conductors 28. The mantle 40 is formed by shrink-mounting a shrink hose or by winding or entwining with one or more threads, wires, bands, or with thread, wire, or band-type devices, for instance.

In a sixth step 106 the inner tube 21 is inserted into an outer tube 22.

Alternatively to clamping the positioning clip 30 on the inner tube 21, in the second step 102 the positioning clip 30 can be inserted into the outer tube 22 and can be attached there by clamping and optionally by cementing, soldering, or welding before the inner tube 21 is inserted into the outer tube 22. Before or during clamping of the positioning clip 30 in the outer tube 22, one or more lightwave conductors 28 can be positioned and at least loosely attached between the inner surface 26 of the outer tube 22 and the positioning clip 30.

What is claimed is:

1. An endoscope comprising:
   an inner tube and an outer tube; and
   a positioning clip having a clamping frame that is configured to elastically deform to clamp the positioning clip in force-fitted connection on the inner tube or in the outer tube, the clamping frame having:
      at least one inner support surface to support the positioning clip on the inner tube;
      at least one outer support surface to support the positioning clip in the outer tube; and
      three links each extending in a radial direction relative to a longitudinal axis of the clamping frame, said three links being separated apart from each other to provide space configured for placement of lightwave conductors between the inner tube and the outer tube, said three links having either the at least one inner support surface or the at least one outer support surface;
   said positioning clip being configured to enclose only partially around an outer periphery of the inner tube from a proximal end to a distal end of the positioning clip;
   wherein either one of:
      the at least one inner support surface is configured to be contiguous in a connecting area with an outer surface of the inner tube, the connecting area including more than half of an outer periphery of a cross-section of the inner tube, the at least one outer support surface comprising three surfaces connected by said three links with the at least one inner support surface, or
      the at least one outer support surface is configured to be contiguous in a connecting area with an inner surface of the outer tube, the connecting area including more than half of an inner periphery of a cross-section of the outer tube, the at least one inner support surface comprising three surfaces connected by said three links with the at least one outer support surface;
   wherein the at least one inner support surface and the at least one outer support surface provide positioning of the inner tube in the outer tube with separation between the tubes.

2. The endoscope according to claim 1, wherein the positioning clip is configured to enclose the inner tube more than halfway.

3. The endoscope according to claim 1, wherein the positioning clip further comprises several inner support surfaces at a distance from one another.

4. The endoscope according to claim 1, wherein the positioning clip further comprises several outer support surfaces at a distance from one another.

5. The endoscope according to claim 1, wherein the positioning clip is configured to enclose the inner tube more than halfway, and said at least one inner support surface and said at least one outer support surface are positioned in a peripheral direction.

6. The endoscope according to claim 1, wherein the links neighboring one another are separated by less than 180 degrees.

7. The endoscope according to claim 6, wherein the links neighboring one another are separated by 120 degrees or less.

8. The endoscope according to claim 1, wherein the links provide support between the at least one inner support surface and the at least one outer support surface.

9. The endoscope according to claim 1, wherein the at least one inner support surface or the at least one outer support surface is larger than the other of the at least one inner support surface or the at least one outer support surface which comprises the at least two surfaces.

10. The endoscope according to claim 1, wherein each of the three links extends linearly out in the radial direction.

11. The endoscope according to claim 10, wherein each of the three links extends perpendicularly relative to one of the at least one inner support surface or one of the at least one outer support surface.

12. A method of positioning an inner tube in an outer tube of an endoscope, said method comprising the steps of:
   clamping a positioning clip on the inner tube or on the outer tube, the positioning clip having a clamping frame configured to elastically deform to clamp the positioning clip in force-fitted connection on the inner tube or in the outer tube, the clamping frame having:
      at least one inner support surface to support the positioning clip on the inner tube;

at least one outer support surface to support the positioning clip in the outer tube; and three links each extending in a radial direction relative to an longitudinal axis of the clamping frame, said three links being separated apart from each other to provide space configured for placement of lightwave conductors between the inner tube and the outer tube, said three links having either the at least one inner support surface or the at least one outer support surface; and positioning the inner tube in the outer tube after clamping the positioning clip, wherein the positioning clip encircles the inner tube only partially and the at least one inner support surface is completely contiguous with the inner tube;

wherein said positioning clip is configured to enclose only partially around an outer periphery of the inner tube from a proximal end to a distal end of the positioning clip;

wherein either one of:

the at least one inner support surface is configured to be contiguous in a connecting area with an outer surface of the inner tube, the connecting area including more than half of an outer periphery of a cross-section of the inner tube, the at least one outer support surface comprising three surfaces connected by said three links with the at least one inner support surface, or the at least one outer support surface is configured to be contiguous in a connecting area with an inner surface of the outer tube, the connecting area including more than half of an inner periphery of a cross-section of the outer tube, the at least one inner support surface comprising three surfaces connected by said three links with the at least one outer support surface; and wherein the at least one inner support surface and the at least one outer support surface provide positioning of the inner tube in the outer tube with separation between the tubes.

13. The method according to claim 12, further comprising the steps of:

positioning a lightwave conductor on an outer wall of the inner tube or on an inner wall of the outer tube before clamping the positioning clip.

14. The method according to claim 12, further comprising the steps of:

bonding the positioning clip with the inner tube or with the outer tube.

* * * * *